US010292777B1

(12) United States Patent
Adelman

(10) Patent No.: US 10,292,777 B1
(45) Date of Patent: May 21, 2019

(54) DEVICE AND METHOD FOR CONTROLLED MOTION OF A TOOL

(71) Applicant: Thomas L. Adelman, Wayne, PA (US)

(72) Inventor: Thomas L. Adelman, Wayne, PA (US)

(73) Assignee: ELYTRA TECHNOLOGIES, LLC, Wayne, PA (US)

( * ) Notice: Subject to any disclaimer, the term of this patent is extended or adjusted under 35 U.S.C. 154(b) by 101 days.

(21) Appl. No.: 15/268,964

(22) Filed: Sep. 19, 2016

Related U.S. Application Data

(60) Provisional application No. 62/220,443, filed on Sep. 18, 2015.

(51) Int. Cl.
| | |
|---|---|
| *G06F 3/01* | (2006.01) |
| *A61B 34/30* | (2016.01) |
| *A61B 34/37* | (2016.01) |
| *A61B 34/00* | (2016.01) |
| *B25J 9/16* | (2006.01) |

(52) U.S. Cl.
CPC .............. *A61B 34/30* (2016.02); *A61B 34/25* (2016.02); *A61B 34/37* (2016.02); *B25J 9/1689* (2013.01); *A61B 2218/00* (2013.01)

(58) Field of Classification Search
CPC .......... A61B 34/30; A61B 2017/00477; A61B 2090/064; A61B 34/70; A61B 34/77; G01C 21/00; G01C 21/20; G06F 3/0346; G06F 3/014; H04Q 2209/43; H04Q 9/00; B25J 9/1664; B25J 9/1671; G08C 2201/32
USPC ................. 700/245, 259, 264; 701/2, 24, 28; 600/109, 411, 439; 606/205, 167
See application file for complete search history.

(56) References Cited

U.S. PATENT DOCUMENTS

| | | | |
|---|---|---|---|
| 4,320,692 A | 3/1982 | Komiya | |
| 4,853,874 A | 8/1989 | Iwamoto et al. | |
| 5,952,796 A | 9/1999 | Colgate et al. | |
| 6,246,200 B1 | 6/2001 | Blumenkranz et al. | |
| 6,424,885 B1 | 7/2002 | Niemeyer et al. | |
| 6,902,560 B1 | 6/2005 | Morley et al. | |
| 7,398,707 B2 | 7/2008 | Morley et al. | |
| 7,689,320 B2 | 3/2010 | Prisco et al. | |
| 7,914,522 B2 | 3/2011 | Morley et al. | |
| 8,528,440 B2 | 9/2013 | Morley et al. | |
| 9,550,293 B2 * | 1/2017 | Hatakeyama | ............... B25J 9/06 |
| 2002/0176683 A1 | 11/2002 | Harman et al. | |
| 2004/0078114 A1 | 4/2004 | Cordell et al. | |
| 2005/0166413 A1 | 8/2005 | Crampton | |
| 2011/0023651 A1 | 2/2011 | Cooper | |
| 2011/0125165 A1 | 5/2011 | Simaan et al. | |
| 2013/0131867 A1 | 5/2013 | Olds et al. | |

(Continued)

OTHER PUBLICATIONS

U.S. Appl. No. 14/213,654 Office Action dated Apr. 20, 2017.

(Continued)

*Primary Examiner* — Dalena Tran
(74) *Attorney, Agent, or Firm* — Pepper Hamilton LLP

(57) ABSTRACT

The present embodiments relate to operator control in a master-slave robotic system, including, but not limited to, wherein an operator uses a master control input device to guide the position and orientation of a tool that is driven by the robotic system. Embodiments described herein provide devices and methods of increasing precision control for complex motions by, for example, decoupling operator control of rotational and translational movement.

20 Claims, 7 Drawing Sheets

(56) References Cited

U.S. PATENT DOCUMENTS

| | | |
|---|---|---|
| 2013/0296884 A1 | 11/2013 | Taylor et al. |
| 2013/0304258 A1 | 11/2013 | Taylor et al. |
| 2014/0005682 A1* | 1/2014 | Worrell ............. A61B 18/1442 606/130 |
| 2014/0277740 A1 | 9/2014 | Adelman |
| 2016/0096271 A1 | 4/2016 | Taylor et al. |
| 2018/0021096 A1* | 1/2018 | Kostrzewski .......... A61B 90/06 |

OTHER PUBLICATIONS

U.S. Appl. No. 14/213,654 Final Office Action dated Nov. 30, 2017.
Notice of Allowance dated May 17, 2018 in U.S. Appl. No. 14/213,654.

\* cited by examiner

DEVICE AND METHOD FOR CONTROLLED MOTION OF A TOOL

RELATED APPLICATIONS

The present application claims priority to U.S. Provisional Application No. 62/220,443, filed Sep. 18, 2015, which is incorporated by reference herein in its entirety. This application is also related to U.S. patent application Ser. No. 14/213,654, filed Mar. 14, 2015, which is incorporated by reference herein in its entirety.

BACKGROUND

The use of surgical robots can offer many advantages over traditional surgery. A common use of such systems is in a master-slave configuration. In such systems, a master control is operated by an operator and used to guide the position and orientation of an end effector located at the end of a robotic arm. In such systems a human operator guides a master control, and the input to this master control is used to guide the slave arm of the robot, and often this guidance is used to direct the motion of an end effector at the distal end of the slave arm.

One potential improvement that such systems may offer over traditional surgery is improved precision at the slave site, and considerable efforts have been made towards this end. One set of challenges of such systems are the limitations of the human operator. Several previous devices methods have been devised to work around, or compensate for, some common and innate human limitations.

Several approaches have been used to improve the precision with which a tool can be guided by an operator. One of these methods is filtering applied to the signal from the master controller aimed at reducing the effects of unwanted movement due to hand tremors on the master control, so that the slave tool moves in a way that is less influenced by the tremors. As tremors may cause unintended motion of the tool, the filtered response of the slave may be more consistent with what was intended by the operator, and in this way filtering applied to the signal from the master controller may act to increase the precision with which the slave tool can be controlled.

However, a disadvantage of filtering is that since multiple sequential sensor readings from the master controller may be required as inputs to the filters, and these readings must be taken over a timescale comparable to the tremor cycle, acquiring these additional inputs can incorporate delays into the system. This can delay the motion of the slave tool and visual feedback times, and make interactive control of the tool more difficult. That is, in master-slave systems, the tool is usually guided in a closed loop configuration, where the operator performs a movement of the master controller and then views the resulting motion of the tool (either directly, through a physical device such as a microscope, or through a camera), and delays in this feedback loop hinder closed loop control.

Another method used to increase precision is scaling, wherein the motions of the master control are transmitted to the slave control at a reduced scale. For example, a motion of the master control of 1 cm might direct the slave tool to move 1 mm. Scaling can result in improved precision control at the site of the slave end effector if an operator can guide the master control so that a system where without scaling would give a precision of 1 mm at the slave site, then a system that has a scale factor of 0.1, the precision at the slave site would be approximately 0.1 mm.

A disadvantage of scaling is that it reduces the spatial extent of the region at the site of the slave end effector that can be easily accessed; specifically, the region that can be accessed using a continuous and linearly scaled motion of the master control will have a range of motion reduced by the same scale factor. For example, if the master control has a 10 cm range of motion and the scale factor remains at 0.1, the range of motion at the site of the end effector will be approximately 1 cm. To get around this problem, it may be possible, for example, to "ratchet" the input, by repeatedly engaging and disengaging the link between the master and slave control (similar to lifting a computer mouse to relocate the physical mouse position relative to the cursor). However, this can become tedious if the surgeon has to ratchet many times. Therefore, it remains advantageous to find other approaches to increasing precision.

Accordingly, there is a continuing need in the art for devices and methods that can provide stable, high-precision controlled motion of a tool. The embodiments disclosed herein addresses these needs and others.

SUMMARY

Embodiments described herein provide devices and methods for controlling the movement of an end effector. In some embodiments, the device comprises a controller, a sensor assembly, a processor, an end effector, and one or more switches, wherein the controller is operatively connected to the end effector to control the rotational and translational movement of the end effector; the processor is operatively connected to the controller and the end effector, wherein the processor is configured to receive one or more inputs from the sensor assembly and to provide a rotational output command and/or a translational output command, based upon the one or more inputs, to the end effector to control rotational movement and/or translational movement of the effector; and the processor is operatively connected to the switches, wherein the switches control output of the rotational output command and the translational output command to control the rotational and translational movement of the end effector.

In some embodiments, methods of moving an end effector in a translational movement that is significantly free of any rotational movement or in a rotational movement that is significantly free of any translational movement, wherein a controller is operatively connected to the end effector are provided. In some embodiments, the methods comprise sensing a force and/or motion input applied to the controller via a sensor assembly; transmitting the force and/or motion input from the sensor assembly to a processor in communication with the sensor assembly; analyzing the force and/or motion input via the processor to decouple the rotational movement and the translational movement into a rotational output command and a translational output command; and transmitting the rotational output command and/or the translational output command to the end effector to move the effector in a translational movement that is significantly free of any rotational movement or in a rotational movement that is significantly free of any translational movement.

In some embodiments, methods of moving an end effector, wherein a device comprising at least a first controller and a second controller are operatively connected to the end effector are provided. In some embodiments, the method comprises sensing a force and/or motion input applied to the first controller and the second controller via a sensor assembly; transmitting the force and/or motion input from the sensor assembly to a processor in communication with the sensor assembly; analyzing the force and/or motion input via the processor to provide a first controller rotational output command, a first controller translational output command, a second controller rotational output command, and a second controller translational output command; and transmitting the first controller rotational output command and/or the first controller translational output command to the end effector to move the effector in a translational movement that is significantly free of any rotational movement or in a rotational movement that is significantly free of any translational movement; and/or transmitting the second controller rotational output command and/or second controller the translational output command to the end effector to move the effector in a translational movement that is significantly free of any rotational movement or in a rotational movement that is significantly free of any translational movement.

DETAILED DESCRIPTION

Figure 1:
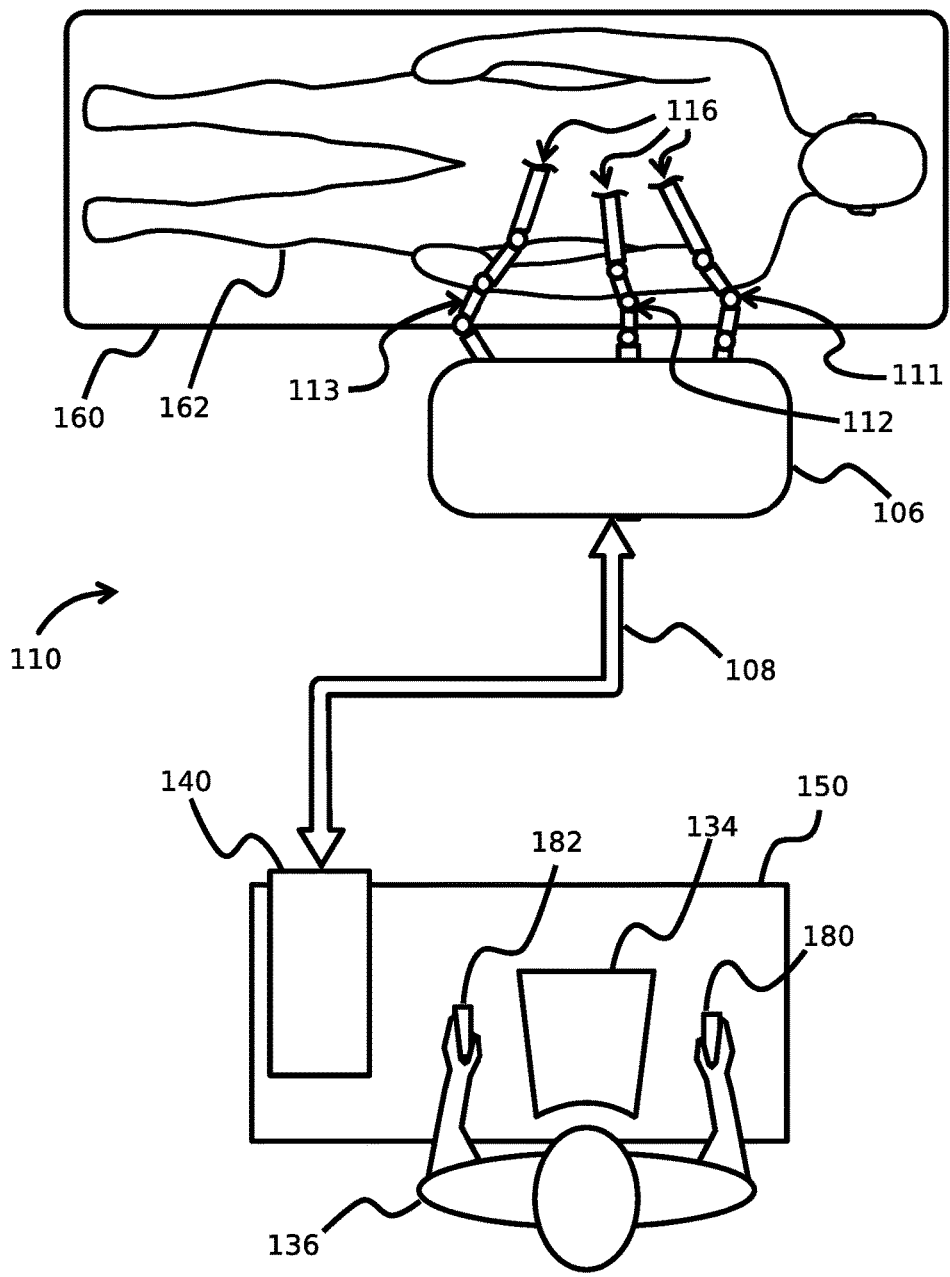
FIG. 1 illustrates a non-limiting schematic representation of an overview of an embodiment, 110, for a telerobotic minimally invasive surgical application.

It is to be understood that the figures and descriptions of the embodiments may have been simplified to illustrate elements that are relevant to some embodiments, while eliminating, for the purpose of clarity, many other elements found in the field of electromechanical devices, robotics, and the like. Those of ordinary skill in the art may recognize that other elements and/or steps are desirable and/or required in implementing some embodiments. However, because such elements and steps are well known in the art, and because they do not facilitate a better understanding of some embodiments, a discussion of such elements and steps is not provided herein nor is it required. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The articles "a" and "an" are used herein to refer to one or to more than one (i.e., to at least one) of the grammatical object of the article. By way of example, "an element" means one element or more than one element, unless context dictates another meaning.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various embodiments can be presented in a range format. It should be understood that the description in range format is merely for convenience and brevity and should not be construed as an inflexible limitation on the scope of the embodiments. Accordingly, the description of a range should be considered to have specifically disclosed all the possible subranges as well as individual numerical values within that range, including the endpoints of the range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments there between.

The embodiments provided for herein provide devices and methods for performing high precision movements. This movement is accomplished, for example, in some embodiments by decoupling the control of rotational and translational movement. By "decoupling" it is meant that an operator of a device can use a controller to control the movement of an end effector but the end effector only moves by a rotation movement or by a translation movement. This "decoupling" can be accomplished, for example, through the use of the sensors (e.g. sensor assembly), processors, and switches as described herein. A sensor assembly can refer to a single sensor or a plurality of sensors. Thus a sensor assembly can refer to one or more sensors. The ability to decouple the movements and allows for fine movements without the disadvantages of the previous attempts to improve precision and movements of devices. The "decoupling" can refer to the commands transmitted to an end effector that enable to the end effector to move by only one of rotation or translation. The decoupling of the movements is described throughout and can have various applications and uses as described herein. Decoupling control also refers to the use of, for example, two controllers, where one controller controls the rotational movement of an end effector and the other controller controls the translational movement of the end effector. Thus, although the end effector can be moved both rotationally and translationally at the same time the movement is decoupled by the controllers to allow for more precision movements. Thus, the term decoupling control of rotational and translational movement can refer to the movement from one controller being switched between a translation or rotation mode as described herein, or where multiple controllers are used to operate each type of movement exclusively, but that the end effector is not limited in its movements either rotationally or translationally.

Embodiments described herein provide many advantages and unexpected benefits over previous methods and devices. The advantages and unexpected benefits described herein are non-limiting and there may be other advantages and benefits apparent to one of skill in the art that are encompassed by the present embodiments.

For example, in some embodiments, one advantage the embodiments described herein can be understood by considering an additional limitation often seen with human control of a tool. An additional source of human control error is due to relative movement errors; that is, it is commonly found that as the length of a hand motion increases, the errors of the motion increase. Put another way, in comparing two precision tasks that differ only in the extent of motion, to attain the same level of precision, the task with the longer extent will generally take more time to complete. For a fixed amount of time taken for a given movement, it is a common experience that a surgical tool moved a short distance can usually be positioned more accurately than a surgical tool moved a long distance in the same length of time. This relates to the human component and can hold even when tool is controlled through a master-slave configuration. This is a problem of "relative precision," in that people can be more precise when guiding a tool using short motions than long motions, in the same span of time.

The problem of "relative precision" becomes particularly apparent when rotating a tool during microsurgery. During such a rotation, the surgeon may often wish to keep the tip of the tool at an approximately fixed location (for example, to avoid damaging tissue in the vicinity of the tip) during the rotation. To effect the rotation though, the handle of the tool must be moved through an arc around this fixed location. Since the length of the arc is usually much larger (often much more than 100 times longer) than the acceptable error in the position of the tip, this may become a problem concerning relative precision. That is, the surgeon needs to move the handle of the tool through an arc much longer than the allowed deviation of the tip of the tool, and the relatively large difference in the sizes of the motion and allowed error can make this very challenging. The present embodiments solve this problem, as well as others described herein. The devices and methods described herein allow for the precision of the tool, by, in part, decoupling the control of rotational and translational movements.

The advantages of the present embodiments, cannot be resolved by linear scaling alone. Comparing motions of the master control, an important ratio is the precision that can be attained in small motions compared with the distance that are required to physically rotate the hand that guides the master control. Because, when scaled, these distances scale together, and the absolute precision that can be attained for fine motion of the tool is degraded during the larger translation.

Embodiments described herein provide for increased precision of tools by decoupling rotational and translational control of a tool, so that directives from the operator control only rotation or only translation of the tip of the tool. These movements can be decoupled so that the operator can, in some embodiments, control one movement (i.e., rotational or translational) but not both simultaneously or with the same force and/or motion. The input control of the embodiments described herein and the resulting motion of the tool that can result from this is generally perceived as intuitive by the operator; and, because the rotations can be done more quickly, the control of the overall task can also be done more quickly without losing precision. Accordingly, in some embodiments, the device and methods allow the user to switch into and out of a pure rotational state and/or a pure translational state, the surgical tool can be relatively easily controlled in this configuration with increased precision and/or speed as compared to previous devices and methods. Decoupling the control of the rotational and translational movements can, in some embodiments, give an improved precision of control of up to 100× or greater and allow for much faster hand motions that require less attention.

In some embodiments, the devices and methods provided for herein are used to perform microsurgery. For example, in microsurgery the tip of the slave tool can be located very close to critical structures, and the device and methods described herein enable an operator (e.g. surgeon) to reposition and reorient the tool with reduced risk to nearby tissue. For example, in suturing a small blood vessel, it might be required to orient the tool appropriately to grasp the suture needle, then orient the tool so that the needle is correctly oriented relative to the tissue, then translate the tool to push the needle through the tissue, etc. The devices and methods described herein can perform these tasks.

In some embodiments, methods and devices described herein are directed to, in part, surgical robotics systems having a master-slave configuration. In such a system the actions of a surgeon (operator) are read by an input device (the master controller) and signals from the input device are used by the robotic processor to direct the motion of one or more robotic arms (the slave). More specifically, in some embodiments, a device and methods are provided that have improved control and guidance of precision motions for a master-slave robotic system.

In some embodiments, the device comprises a human input device, or HID (often the master controller of a robotic master-slave system); a robotic arm, typically having an end effector; a robotic processor; and a viewer device for the surgeon to view the end effector. In some embodiments, the device can be used for tasks where precisely guided motion of the robotic arm and end effector is required for some aspects of a procedure. In some embodiments, the robotic processor is configured to receive input from the HID and generate output that guides the position and movement of a robotic arm.

Although some of these components may already be largely known, the configurations described herein have not been previously described. In some embodiments, the device is configured to create a system and perform methods for which various aspects are particularly well suited for performing tasks at high precision. The system can also be configured to operate without the high level of precision.

Accordingly, in some embodiments, devices and methods for moving end effectors are provided, including, but not limited to those that are described herein or equivalent variants thereof.

In some embodiments, a device comprising a controller, a sensor assembly, a processor, an end effector, and one or more switches is provided. In some embodiments the controller is operatively connected to the end effector to control the rotational and translational movement of the end effector. In some embodiments, the processor is operatively connected to the controller and the end effector, wherein the processor is configured to receive one or more inputs from the controller and to provide a rotational output command and/or a translational output command, based upon the one or more inputs, to the end effector to control rotational movement and/or translational movement of the end effector. In some embodiments, the processor is operatively connected to the switches, wherein the switches control output of the rotational output command and the translational output command to control the rotational and translational movement of the end effector.

The processor can be any processor suitable to receive one or more inputs and transmit one or more outputs. In some embodiments, the processor is a microprocessor. Thus, the microprocessor can be any microprocessor suitable for processing data from a sensor or sensor assembly along with any other sensors or inputs from the device. In addition, the microprocessor can be any microprocessor suitable for controlling the end effector. In some embodiments, the processor can be connected to the other components of the device via wires. In some embodiments, the processor can be connected to the other components wirelessly, for example via WiFi or Bluetooth.

In some embodiments, the processor is configured to determine the rotational and translational movement of the controller and the processor is configured to communicate with the end effector to move the end effector in a rotational movement and/or a translational movement. In some embodiments, the processor is configured to communicate with the end effector to move the end effector in a rotational movement that is significantly free of any translational movement. In some embodiments, the processor is configured is configured to communicate with the end effector to move the effector in a translational movement that is significantly free of any rotational movement.

In some embodiments, the one or more of the switches are configured to select one of the rotational command and the translational command to control movement of the end effector. The switch can be any type of switch suitable for such configuration. Examples, include, but are not limited to a foot switch, finger operated switch, a graphical user interface, a touch system, a voice recognition systems, or any combination thereof. One can also use a device such as a mouse to toggle the one or more switches. The switches can also be used to toggle the different modes of the device that are described herein.

In some embodiments, the sensor assembly is configured to measure the revolute displacements and/or the linear displacements of the controller. This enables the sensor assembly to transmit to the processor the different rotational and translational outputs so that the rotational and translational control can, for example, be decoupled as described herein.

For example, in some embodiments, the one or more switches are configured so that the end effector rotational movement is significantly free of any translational movement. In some embodiments, the end effector rotational movement is less than 5 mm, 1 mm, 0.5 mm, 0.2 mm, 0.1 mm, 0.05 mm, 0.02 mm, 0.01 mm, 0.005 mm, 0.002 mm, 0.001 mm, 0.0005 mm, or 0.0002 mm of translation of the end effector. In some embodiments, the one or more switches is configured to so that the effector translational movement is significantly free of any rotational movement. In some embodiments, the end effector translational movement has less than 20, 19, 18, 17, 16, 15, 14, 13, 12, 11, 10, 9, 8, 7, 6, 5, 4, 3, 2, 1, 0.3, 0.1, 0.03, 0.01, 0.003, or 0.001 degree of rotational movement. The switches can control the movement of the end effector based upon a plurality of controllers as described herein. For example, a device could comprise one controller that controls rotational movement and another controller that controls translational movement. Thus, the switches can be used to control what is communicated from the plurality of controllers to the end effector to enable precision movement in view of the decoupled control.

Therefore, in some embodiments, the controller is operatively connected to the end effector in a translation mode and/or rotation mode. The controller can be operatively connected to the end effector via the sensors, processors, and/or switches. In some embodiments, the device is configured such that a force or motion applied to the controller moves the end effector through pure translation. In some embodiments, the device is configured such that a force or motion applied to the controller moves the end effector translationally and the end effector has less than 20, 19, 18, 17, 16, 15, 14, 13, 12, 11, 10, 9, 8, 7, 6, 5, 4, 3, 2, 1, 0.3, 0.1, 0.03, 0.01, 0.003, or 0.001 degree of rotational movement.

In some embodiments, the device is configured such that a force and/or motion applied to the controller moves the end effector through pure rotation. In some embodiments, the device is configured such that a force and/or motion applied to the controller moves the end effector rotationally and the end effector has less than 5 mm, 1 mm, 0.5 mm, 0.2 mm, 0.1 mm, 0.05 mm, 0.02 mm, 0.01 mm, 0.005 mm, 0.002 mm, 0.001 mm, 0.0005 mm, or 0.0002 mm of translation of the end effector.

The controller can be any controller that can be used to control the movement of an end effector. The exact form of an end effector is not critical, but rather the end effector can be designed for the operation or use. In some embodiments, the controller is a grip. In some embodiments, the grip is a rigid grip. In some embodiments, the controller comprises a system of connecting elements and movable joints that allow the grip to be moved in six degrees of freedom (6-DoF) where three degrees of freedom (3-DoF) correspond to the position of the controller, and 3-DoF correspond to the orientation of the controller. In some embodiments, the grip is a device that has three degrees of freedom (3-DoF).

The device can also comprise a sensor assembly that is configured to receive inputs from the controller to determine the position of the controller and the orientation of the controller. In some embodiments, the processor is configured to receive inputs from the sensor assembly to determine the rotational movement of the controller and/or the translational movement of the controller. The inputs can then be used to transmit outputs from the controller to the end effector. Therefore, in some embodiments, the processor is configured to output the rotational movement of the controller and/or the translational movement of the controller to the end effector to move the end effector in a rotational movement and/or translational movement.

The processor can transmit to the end effector through any suitable means of communication. The processor can transmit through one or more communication channels. For example, in some embodiments, the processor is configured to output the rotational movement of the controller to the end effector through a first communication channel. In some embodiments, the processor is configured to output the translational movement of the controller to the effector through a second communication channel. The transmission through the communication channels can be controlled, for example, by the one or more switches. Thus, in some embodiments, the one or more switches are configured to prevent transmission through the first and/or second communication channel.

In some embodiments, the processor is configured to output the rotational movement of the controller and/or the translational movement of the controller to the end effector to move the end effector in a translational movement that is significantly free of any rotational movement. In some embodiments, the processor is configured to output the rotational movement of the controller and/or the translational movement of the controller to the end effector to move the end effector in a rotational movement that is significantly free of any translational movement. In some embodiments, the device is configured to move the effector in a rotational movement that is significantly free of any translational movement. In some embodiments, the device is configured to move the end effector in a translational movement that is significantly free of any rotational movement. The configuration can be done through the use of switches, programming, or configuration of sensors.

Accordingly, in some embodiments, the one or more switches configures the device to move the end effector in a rotational movement that is significantly free of any translational movement. In some embodiments, the one or more switches configures the device to move the end effector in a translational movement that is significantly free of any rotational movement. These different movements can be from one or more controllers as described herein. Thus, a device, or system, that has two controllers can have two different operations occurring simultaneously. In one instance, one controller is controlling the rotational movement of the end effector and another controller is controlling the translational movement. Thus, the end effector may be moving in both rotation and translation, but each controller is uniquely directing, or guiding, the end effector in only one manner, either rotation or translation.

As described herein, the devices, or systems, can be configured to have different modes of operation. In some embodiments, the device comprises a first switch and a second switch, wherein the first switch configures the device to be in a general mode or a precise mode and the second switch configures the device to be in a rotation mode or a translation mode. End effector refers to what is being controlled by the controller. For example, this can be a robotic arm, or the distal part of a multi jointed robotic arm. The robotic arm can also comprise or be attached to scissors, scalpel, knife, clamp, needle, drill, or syringe. The end effector need not have what is generally recognized as a robotic arm and instead simply have a holder that holds another instrument such as, but not limited to, those described herein. These are non-limiting examples of end effectors and others can be used or be part of the device (system).

The present disclosure also provides for methods of moving end effectors. In some embodiments, the methods are methods of moving an end effector in a translational movement that is significantly free of any rotational movement, or in a rotational movement that is significantly free of any translational movement, wherein a controller is operatively connected to the end effector. In some embodiments, the method comprises sensing, via a sensor assembly, a force and/or motion input applied to the controller; transmitting the force and/or motion input from the sensor assembly to a processor in communication with the sensor assembly; analyzing the force and/or motion input via the processor to produce a rotational output command and a translational output command; and transmitting the rotational output command and/or the translational output command to the end effector to move the effector in a translational movement that is significantly free of any rotational movement or in a rotational movement that is significantly free of any translational movement. The method can be implemented by using any of the devices described herein. In some embodiments, herein the controller is associated with a device comprising one or more switches, wherein the one or more switches are configured to control the transmission of the rotational output command and/or the translational output command, wherein the one or more switches prevent the transmission of the rotational output command and/or the translational output command to the end effector.

In some embodiments, methods of moving an end effector, wherein a device comprising at least a first controller and a second controller are operatively connected to the end effector are provided. In some embodiments, the method comprises sensing a force and/or motion input applied to the first controller and the second controller via a sensor assembly; transmitting the force and/or motion input from the sensor assembly to a processor in communication with the sensor assembly; analyzing the force and/or motion input via the processor to decouple the rotational movement and the translational movement from the first controller and the second controller into a first controller rotational output command, a first controller translational output command, a second controller rotational output command, and a second controller translational output command; and transmitting the first controller rotational output command and/or first controller the translational output command to the end effector to move the effector in a translational movement that is significantly free of any rotational movement or in a rotational movement that is significantly free of any translational movement; and/or transmitting the second controller rotational output command and/or second controller the translational output command to the end effector to move the effector in a translational movement that is significantly free of any rotational movement or in a rotational movement that is significantly free of any translational movement. In some embodiments, the device is configured to transmit only one of the first controller rotational output command and/or first controller the translational output command to the end effector. In some embodiments, the device is configured to transmit only one of the second controller rotational output command and/or second controller the translational output command to the end effector. In some embodiments, the device only transmits the first controller rotational output command and the second controller translation output command to the end effector to move the end effector.

The methods described herein can be implemented by one or more of the devices or systems described herein that are configured to implement or perform the methods.

The embodiments described herein are non-limiting. Other embodiments are provided for herein, such as those described/illustrated in the Figures.

For example, FIG. 1 shows a non-limiting schematic representation of an overview of some embodiments, 110, for a telerobotic minimally invasive surgical application. Here, a surgeon 136 is seated at a station 150 and is controlling the device using two master controllers 182 and 180. Signals from these controllers are transmitted to a processor 140, signals from the processor are sent via channel 108 to a surgical robot 106 which controls one or more articulated robotic arms, shown here as 111, 112, and 113. In some embodiments, the articulated arms have a portion that enters a patient 162 through incisions at 116. The articulated robotic arms can control tools, cameras, or other items. In some embodiments, the camera can be used to send a stereoscopic video back through channel 108, or a different channel, where it can be viewed by the surgeon 136 through viewer 134.

Figure 2:
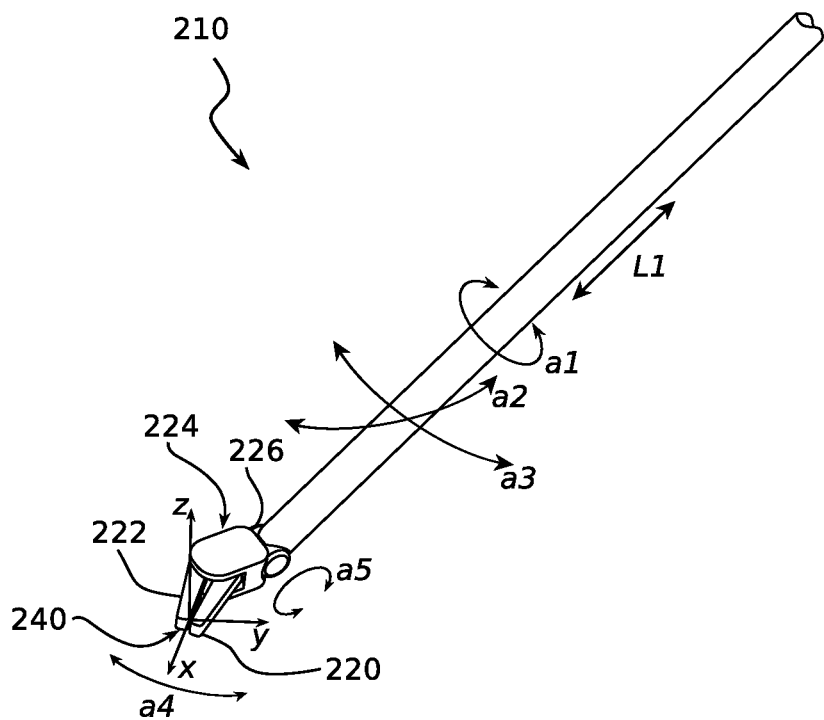
FIG. 2 illustrates a schematic of a non-limiting example of a tool and end effector, as could be attached.

FIG. 2 illustrates other embodiments. FIG. 2 shows a schematic of a non-limiting example of a tool and end effector, as could be attached, for example, to arm 111. An example of such a tool includes, but is not limited to, an EndoWrist by Intuitive Surgical. This tool is used here as a non-limiting example of tool, here, one that can be moved in six degrees of freedom (6-DoF) allowing it to achieve many different positions and orientations while under robotic control, even when inserted through a fixed small incision in the patient. The tool achieves these degrees of freedom by motion through the angles a1-a5 shown, and changing the insertion length L1. Other examples of surgical end effectors include, but are not limited to, clamps, graspers, scissors, staplers, or needle holders, for example, that generally can be manipulated to sever, grasp, cauterize, irradiate and suture tissue, for example. Here it will be appreciated that movement of the end effector, both in position and orientation of elements 222 and 220, are controlled by appropriately positioned actuators, e.g., electrical motors, or the like.

It should be understood that the embodiments described herein are not tied to any particular robotic arm, tool, and/or end effector described herein; nor limited to end effectors with 6-DoF. The tools and systems described herein are merely used to illustrate various embodiments described herein. Furthermore, in some embodiments, the surgeries may not be telerobotic and/or minimally invasive. The methods and devices described herein can also be applied to non-surgical applications as well.

FIG. 2 shows a Cartesian coordinate reference system 240 attached to the end effector. It should be understood that this is not part of the device, but a mathematical construct. Cartesian coordinate reference systems referenced below will be referred to using the shortened term "frames." The frame is considered to be attached to the object at a point, and rotates and translates with the object, and an attached frame is a generally useful construct, commonly used to describe the position and orientation of an object in space. The origin point of a frame (that is, the intersection of the x, y, and z-axes) does not need to be located on the object for the frame to be attached to that object; by attachment it is meant that the frame and the object move together. For example, if a frame is attached to an object and the frame undergoes pure rotation, the object will rotate with a fixed point (that is, a point of the object that will not move through space) at the origin of the frame. It should also be understood that rotations of a frame are considered as rotations about the origin of the frame.

In some embodiments, the devices and methods provided for herein provide a method of hand-directed precision control of the motion of an end effector. In some embodiments, the hand-directed control is done by the manipulation of one or more master controllers guided by one or more of the surgeon's hands. In some embodiments, the control of a single master controller is controlled by a single hand. However, in some embodiments, another master controller can also be used to control one or more additional tools with the other hand.

As used herein, "guiding frame" refers to the directed motion of the master controller as directing a frame attached to the master controller. For example, an action by the surgeon in the x-direction for a guiding frame attached to grip 180 will result in the end effector moving in the x-direction defined by the frame attached to it (the guided frame). It is not generally required that the guiding frame and the guided frame line up in any absolute sense, that is, for example, that they both have the same orientation relative the surgical theater. In some embodiments, the operator can visualize the guiding and guided frames as being aligned, which can be accomplished using a camera referenced control in a minimally invasive surgical apparatus, which is described in U.S. Pat. No. 6,424,885, which is hereby incorporated by reference. However, this type of camera is not required.

In some embodiments, the master control (e.g. controller) comprises a grip, such as but not limited to a substantially rigid grip, that is mounted to a system of connecting elements and movable joints that allow the grip to be moved in six degrees of freedom (6-DoF) where 3-DoF (three degrees of freedom) correspond to the position of the tool, and 3-DoF correspond to the orientation of the tool. In some embodiments, the connecting elements are rigid connecting elements. One or more additional degrees of freedom may be used to operate the end effector of the tool or other operations, such as closing a scissors, hence, for example, bringing the total to 7-DoF or more. Such controllers are known in the art and include, for example, the Da Vince machine master controller; the PHANTOM Omni (SensAble, USA); RAMS (Robot-Assisted Micro-Surgery); thesis by Raimondo Cau, Eindhoven University of Technology, 2013.

Figure 3:
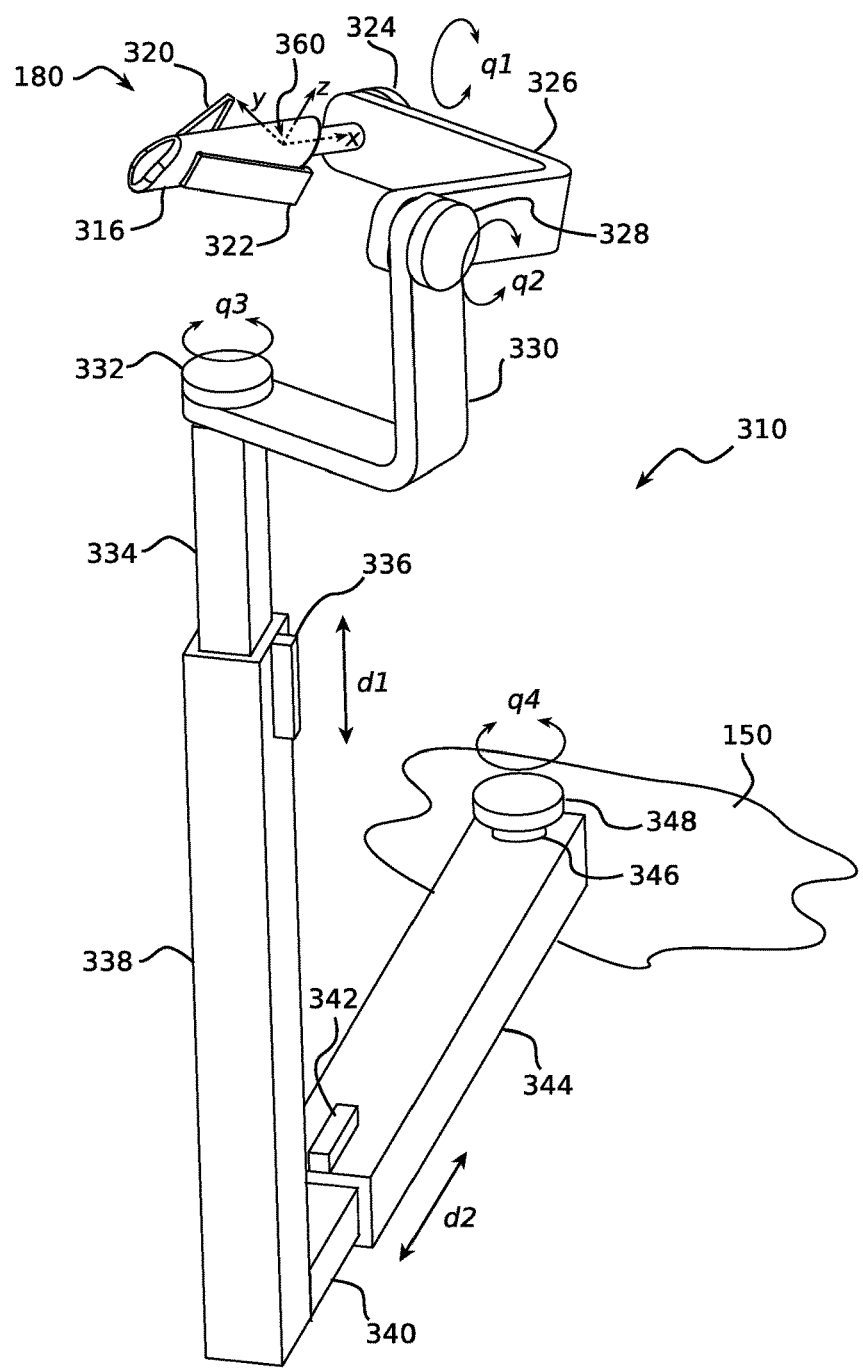
FIG. 3 illustrates a diagram of a non-limiting example of a master controller.
Figure 4:
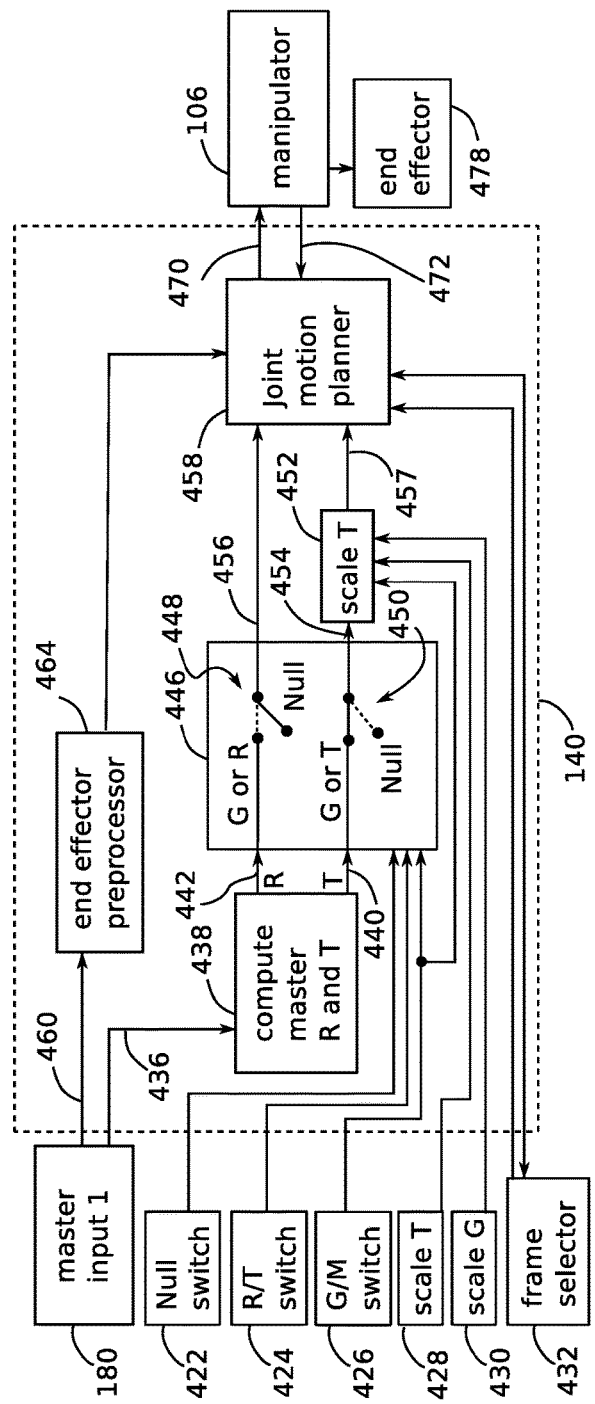
FIG. 4 illustrates a non-limiting schematic representation of an overview of an embodiment

FIG. 3 illustrates other embodiments. FIG. 3, for example, shows a diagram of a non-limiting example of a master controller 310, and FIG. 4 shows a non-limiting schematic of the processing involved in this system for reading values from the master controllers and mapping these to the motion of the slave tools. For example, the operator can grasp grip 180. In some embodiments, the grip comprises the main body of the grip 316, and two lever controls 320 and 322. In some embodiments, the master controller comprises revolute joints 324, 328, and 332. These can, for example, allow the surgeon to change the orientation of the grip 180. In some embodiments, the grip can also translate by the movement in prismatic joints formed by the linear sliding of element 334 within element 338, which houses or encases 334 and the linear sliding of element 340 within element 344, which houses or encases 340, and additionally through the revolute joint formed by the rotation of component 344 about 346. The axis of joint 346 can, in some embodiments, be attached to the universal frame 350 in which the surgeon is stationary, for example, the operating theater.

In some embodiments, the controller comprises one or more sensors. The sensors can be in a sensor assembly. A sensor assembly can have only one sensor if that is all that is needed. In some embodiments, the controller comprises 1, 2, 3, 4, 5, 6, 7, 8, 9, or 10 sensors. The sensors can be configured to measure the revolute displacements and linear displacements between various components of the controller as illustrated in FIG. 3. As illustrated in FIG. 3 a controller can comprise sensors 324, 328, 332, 348, 336, and 342. The sensors can be configured to measure the revolute displacements between components 316 and 326, 326 and 330, 330 and 334, and 344 and 150, and the linear displacements between 334 and 338, 340 and 344, respectively, and the output of these sensors relate to the values for q1, q2, q3, d1, d2, and q4, respectively, herein and below referred to as the master positional joint values. These values are represented, for illustration purposes only, in FIG. 4 by channel 436. The master positional joint values can then be used to guide the motion of the end effector 478. In addition to master positional joint values 436, the values from the sensors at the control levers 320 and 322 can also be sensed, and these are transmitted in channel 460.

In some embodiments, the sensors are configured to extract sufficient information from the master controller to direct the motion of the slave tool end effector 478 in a way such that at least one aspect of a decoupled mode can be used. The decoupled mode has at least one of two aspects: 1) a rotation mode (R-mode), where a subset of applied forces and/or motions of the controller serve to direct the slave tool in a rotational movement; and, 2) a translation mode (T-mode), where a subset of applied forces and/or motions of the controller serve to direct the slave tool through a translation movement. In some embodiments, the rotational movement is significantly free of any translational movement. In some embodiments, rotational movement is free of any translational movement. This can also be referred to as "pure rotation." In some embodiments, the translational movement is significantly free of any rotational movement. In some embodiments, translational movement is free of any rotational movement. This can also be referred to as "pure translation." Throughout this document, by "pure translation" and "pure rotation" of the end effector, refers to the manner in which the directional commands are input by the surgeon and interpreted by the controller, and these phrases should not be interpreted in a limiting way. For example they should not be interpreted so as to imply perfect pure translational and/or perfect pure rotational implementation at the slave site; for it is to be understood that vibrations, limitations in actuator control, limitations due to the slave tool's workspace, and other elements, may all impact the actual translation and rotation of the end effector. In some embodiments, the translation is pure when there is less than +/−20, 19, 18, 17, 16, 15, 14, 13, 12, 11, 10, 9, 8, 7, 6, 5, 4, 3, 2, 1, 0.3, 0.1, 0.03, 0.01, 0.003, or 0.001 degree of rotation. In some embodiments, the rotation is pure when there is less than $\pm 1/10$th, $1/20^{th}$, $1/50^{th}$, $1/100^{th}$, $1/200^{th}$, $1/500$, $1/1000$, $1/2000$, $1/5000$, $1/10000$, $1/20000^{th}$, $1/50000^{th}$, $1/100000^{th}$, or less, of the control span of translation of the end effector; wherein the "control span" is the average maximum distance the slave tool can be guided to move by a single unidirectional and continuous motion, or by a constant force applied for 10 seconds, within the linear control range of the master controller; or the rotation is pure when there is less than 5 mm, 2 mm, 1 mm, 0.5 mm, 0.2 mm, 0.1 mm, 0.05 mm, 0.02 mm, 0.01 mm, 0.005 mm, 0.002 mm, 0.001 mm, 0.0005 mm, 0.0002 mm of translation of the end effector.

The rotation and translation descriptions of the slave tool refer to the motion of the slave tool relative to a universal frame, or more practically described as, for example, the stationary frame of 160 in FIG. 1. By pure rotation about a fixed point, it is meant that if a frame is attached to the end effector, then there exists a point that is approximately stationary in both the universal frame and the end effector frame. For example, for microsurgery, the stationary point is often located on the tool or within about 5 mm from the tip of the tool. In pure translation, the origin of the end effector frame is moved while all axes remain approximately parallel to the axes of the initial frame, and all of the points on the end effector (that form a solid portion containing the point on which the frame is attached) are moved in space by approximately the same vector.

In some embodiments, to extract information to guide the slave tool end effector, a frame 360 is attached to a grip portion 316. In FIG. 3, the guiding frame 360 has the x-axis parallel to the long axis of the grip portion 316, and the z-axis parallel to the resting vertical position. The frame that is attached to the grip can be referred to as the "guiding frame," since its position, orientation, and related motion, is used to guide the position, orientation, and related motion of the end effector. The translation and rotation of this guiding frame can be determined using standard forward kinematics (as discussed in many robotics texts, for example, Introduction to Robotics by John J. Craig, Chapter 3, which is hereby incorporated by reference). In many formulations of forward kinematics calculations, such as that presented by Craig, the rotation and translation of the frame is the usual result of the homogenous transform representation, so that finding the rotation and translation of the frame can be determined for a system such as that presented here, where the frame is connected to a series rigid elements connected at well-defined joints.

It should also be observed here that the rotation and translation of the grip frame can be determined by the forward kinematics calculation, but is not, always or necessarily, directly read from the master positional joint values 436 and cannot, in general, be directly read from the sensors. For example, in system 310, it should be clear that rotation about joint 346 will both translate and rotate the grip frame 360, so that although this system provides a full 3-DoF for translation and 3-DoF for rotation, translation and rotation are not clearly distinguished by independent readings from the joints. For example, not only q1, q2, and q3 are important for determining the rotation of the grip, but also q4. Therefore, to treat rotation and translation differently, it is generally necessary for the processor to be configured in a manner to do a calculation to separate rotation and translation from the direct sensor data. In some embodiments, a master controller is constructed wherein this is not required and the rotation and translational components can be separated by sensor groups. However, the separation of the sensor groups is not required because the movements can be separated by calculation.

The forward kinematics calculation can be carried out in 438, which outputs values, for example, in two independent channels, one channel 440 representing the rotational information and one channel 442 representing the translational information. That is, subprocess 438 in FIG. 4 can take the master positional joint information channel 436, and output the rotation and translation of the master grip frame into two independent channels, 440 for translation information and 442 for rotational information, and this information is passed to the mode selector 446. It should be understood that the values from the sensors are being produced in real time, and that these times are known by the processor, so that using the sensor data and the known times can give both absolute, differential, and velocity information for both the translation and rotation of the frame 360, and this information is passed along through their respective channels 442 and 440.

In some embodiments, the operator can use the switches 422, 424, and 426 to select a current operating mode of the system. Switch 426, for example, represents a toggle switch that selects whether the system is in the generalized control mode (G-mode), wherein both rotation and translation of the end effector can be controlled and varied by continuous variation of a set of input forces; or a decoupled mode (here represented by an "M" representing a "microsurgical setting"). When switch 426 is in the decoupled state, switch 424, a toggle switch, can, for example, be used to select between the R-mode and the T-mode. Switch 422 can then be set to a Null-mode for the system in which input from the master positional joint values 436 do not change the position of the end effector, effectively overriding the settings of the other switches. Thus, the system is configured in such a manner to allow decoupled control of rotational and translational movements.

In some embodiments, the mode selector 446 takes input from user operated controls, here represented by the non-limiting example of three switches 422, 424, and 426, to select which information will be passed on to control the end effector. Schematically this is represented by setting internal switches on either channel 448 and 450 to transmit the information contained in the channel unmodified, or to pass a Null value when the switch in the Null-state position. Passing a Null value will be interpreted so that the channel having the Null value will not cause any motion of the end effector.

As shown, the mode selector 446 can have, for example, four states. 1) Null-mode: when both internal switches 448 and 450 are set to "Null", moving the master control will not cause the system to change either the position or orientation of the end effector; this state is active when switch 422 is set to the active setting. For the following modes to be active, switch 422 must be set to the inactive state. 2) G-mode: internal switch 448 is set to the "R" position and 450 is set to the "T" position; this state is active when switch 426 is in the "G" state; G-mode allows simultaneous control of both the rotation and translation of the end effector frame. For the other two modes, that is, the decoupled modes, switch 426 is set to the "M" position. 3) R-mode: internal switch 448 is set to the "R" position and internal switch 450 is set to the "Null" position; this state is active when switch 424 is set to the "R" state; and in this state, the end-effector frame will only move pure rotation. 4) T-mode: internal switch 450 is set to the "T" position and internal switch 448 is set to the "Null" position; this state is active when switch 424 is set to the "T" state and, in this state, the end effector frame will only move in pure translation. The logic for this given the inputs from switches 422, 424, and 426, is built into the mode selector 446 in this embodiment.

Furthermore, when switching out of Null state on either channel, the guiding frame 360 can have changed in both rotation and translation since the time when the Null position was entered into for the channel. It some embodiments, it is undesirable for the end effector to receive a command to quickly move from one position to another position due to this difference in states, so the state of the channel should be recorded when the Null state is entered for a channel, and then only the difference from state after the Null state is left are reported for each channel when the Null state is left.

An exception to the action of the Null-mode, is that while in Null-mode, and as may be selected by the user, and if available in the motion of the system, the levers 320 and 322 may still cause to end effectors 220 and 222 to move relative to the body 224, while the remaining joints in the slave arm remain stationary. This may be useful, for example, during delicate grasping operations where it would be desired to not accidentally move the slave tool while its end effectors are being closed to grasp.

In some embodiments, translation information is transferred from the mode selector 446 via channel 454 to the scaling element 452. A benefit of scaling is that the end effector can respond in a scaled way, for example, for a scaling factor of 0.1, a motion of 1 cm of the grip 180, might be mapped to a motion of 1 mm for the end effector. Accordingly, devices described herein can be configured to also operate using a scaling element. This can aid in guiding precise motion. It should be understood that the T-mode and G-mode might be used for different types of surgical activities, and might benefit from different scaling factors. To this end, independent controls 428 and 430 can be used to set the scaling factors independently, and scaling element 452 can read the state of switch 426 to determine which scaling factor to use. In Null-mode and R-mode, channel 454 will contain a Null value, which is not scaled but just passed through.

Scaling can be accomplished by any method that is appropriate. For example, how scaling is accomplished numerically depends exactly on how the translation information is represented in the system, and is generally known in the art. If, for example, the translation information is represented in a common differential vector form, the scaling can be accomplished simply by multiplying each element of the differential translation vector by a constant scaling factor, and this embodiment, this would depend on the whether the system is in T-mode or G-mode.

In some embodiments, scaling is linear and equal along each axis, although neither of these restrictions are required or limiting in scope. U.S. Pat. No. 4,853,874, which is hereby incorporated by reference, for example, describes how scaling could be different for each axis, and herein, this could most directly refer to the axes of the guide frame 360. This is merely used as a non-limiting example and other methods and elements for scaling can be used.

In some embodiments, as described herein, 438, 446, and 452, take forces applied to the controller and/or the motion of the guiding frame 360, and effectively modify it in a few simple ways to create a conceptual intermediate guiding frame (IGF). More descriptively, in defining the motion, it is useful to consider initial and final states of the IGF between two successive sensor readings from the controller, and consider how these are modified depending on the modes and scale factors. For example, in some embodiments: 1) in T-mode, the initial and final IGFs will only be translated relative to each other but not rotated, so that all axes remain parallel but may be shifted, and the extent of translation of the IGF may be scaled relative to the guiding frame 360 by the setting of 428; 2) in Null-mode both IGF frames will be effectively identical; 3) in R-mode, the final IGF is only rotated relative the initial IGF, and the origins of the initial and final IGFs remain at the same location; 4) in G-mode, the final IGF may be both translated and rotated relative to the initial, and the amount of translation may be scaled relative to the translation of the guiding frame 360 by the setting of 430. Therefore, the change between the two IGF states can be used to guide the end effector to make a similar transition. It should be understood that whereas this description has been in terms of incremental differences of the guiding frame, other approaches can be used to determine the motion of the end effector: both other measurements could be used, for example, the rotational and/or linear velocities, accelerations, and the like, and other calculations, such as using the absolute positions and orientations, the positions and orientation relative to reference positions and orientations, and/or other variations of these and other these quantities.

In some embodiments, to describe how the end effector is guided by the robotic processor 140 a frame, 240, can be attached to the end effector as shown in FIG. 2. This frame will herein be referred to as the guided frame. Given the input from the master controller and the processing described hereinbefore it is known how the guided frame (and associated end effector) should be moved, and the task of the joint motion planner 458 is to determine the motion of the joints of the articulated robot arm that will achieve this goal. That is, for example, in some embodiments, the joint motion planner 458 receives the modified rotational and translational information on channels 456 and 457, based on the guided master controller grip frame 360 (with added adjustments and scaling from 438, 446, and 452) and determines how to move the joints of the slave arm to create the directed motion at the end effector, specifically, by controlling the guided frame.

In general, the problem of calculating the joint positions and speeds required to produce a desired frame position, orientation, and motion is known as "inverse kinematics" and is generally a more difficult problem than the forward kinematics problem described hereinbefore. Solutions of the inverse kinematics for the robotic arm and end effector of the embodiment shown in, 210, are known in the art and can be used to perform this calculation. [U.S. Pat. No. 6,424,885, U.S. Pat. No. 7,689,320 and references therein]. However this and other systems, analytic solutions, iterative numerical solutions, dynamic simulations, pre-calculated lookup tables, and the like, can be used. This is a problem that has practical and working solutions, and it is not the purpose of this document to list an exhaustive list and other solutions can be used. Which of these is used depends on factors such as the computational power available, the articulation of the slave arm, the end effectors, the physical requirements of the system and surgery, and different solutions can take into account factors such as the various conditions that may be required to be met, such as the system might need to have a fixed point where the tool enters the body 116 and other requirements such as limiting the joint speeds or end effector speed; or limiting the range of motion of the end effector.

Information used to guide the slave joint positions and velocities can then be sent from the joint motion planner 458 to the joint manipulator 106 which finally controls the end effector 478. In some embodiments, channel 472 may communicate information about the robotic arm to the joint position planner 458, including the details of the end effector. Other information can be communicated through channel 472, such as ongoing joint position updates, and the like.

Figure 5A:
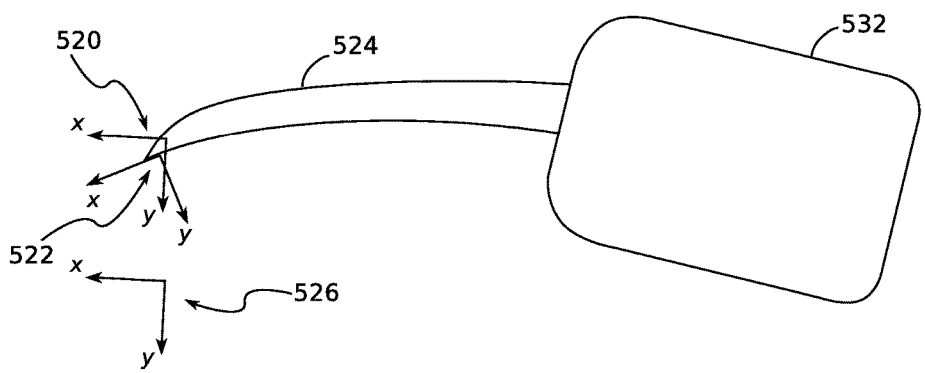
FIG. 5A illustrates a non-limiting example of an end effector.
Figure 5B:
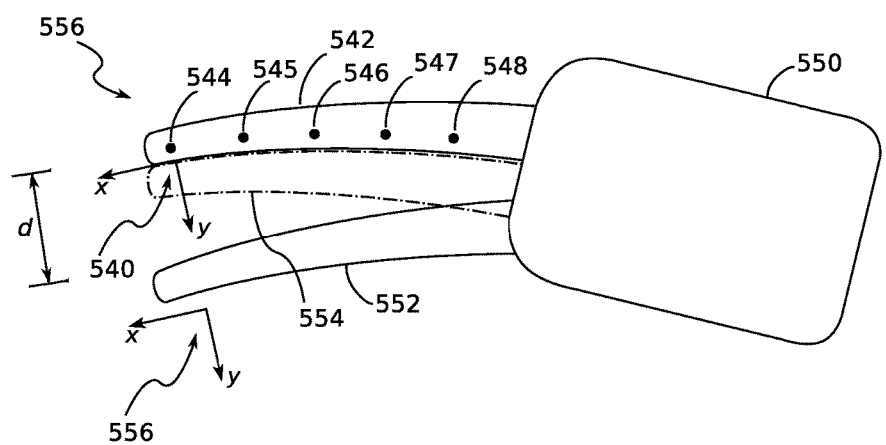
FIG. 5B illustrates a non-limiting example of an end effector.
Figure 5C:
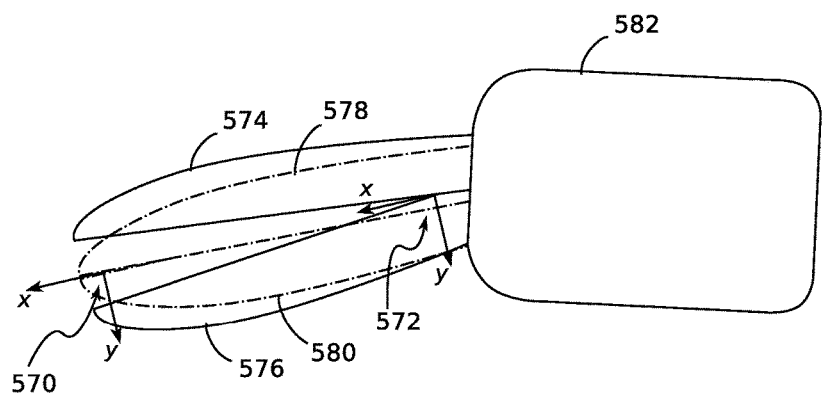
FIG. 5C illustrates a non-limiting example of an end effector.

In some embodiments, the location and behavior of the guided frame of the end effector can improve the precision and operability of the system. In some embodiments, in microsurgery, the end effector can be large relative to critical distance in the surgery, so precise control over the motion of the end effector can yield better and more definite control. FIGS. 5A-5C illustrates examples of several categories of tools and are examples of how frames can be attached to each. All of these illustrations show a view down the z-axis in FIG. 2, and the z-axis is not shown in FIGS. 5A-5C but is coming out of the page towards the viewer (as would be determined by the "right hand rule"). It should be understood that the embodiments described herein are not limited to aspects of these example attachment points or methods.

For example, FIG. 5A shows a simple rigid tool 524 such as a blade or pin, with no relatively moving parts to the end effector. Frame 520 illustrates a frame attached to the tip, with the x-axis approximately aligned along the long axis of the tool. That is, when the system is in T-mode and the grip 316 is moved forward (i.e., along the x-axis of guiding frame 360), the end effector will move in the direction of the x-axis. Another possible location is 522 where the origin is near the tip, but with the x-axis aligned with the tangent of the leading edge. In each of the previous two example 520 and 522, in R-mode, rotations will be about the origin of the guided frame, and here about the points near the tip of the tool. Finally, 526 illustrates an example where the origin of the attached frame is not on the tool, but spaced from it by a small amount. For 526, the T-mode behavior is similar to 520 but in R-mode the motion will be around the origin of frame 526, which could be useful, for example, to score a circle.

FIG. 5B shows an example having an end effector with two movable elements, 542 and 552, which could, for example, represent the jaws of a grasper, and can be moved by the controller in relation to 550 by robotic control. Herein below, the movable elements 542 and 552 will be referred to as "jaws" for convenience. Although not required, it is useful to visualize this tool being used in a circumstance wherein the distance, d, representing the opening width of the jaws, is significantly larger than various critical distances at the surgical site; and by this example, it should be understood that how the jaws move relative to the guiding frame can be an important factor in controlling the end effector. As the jaws can move relative to the guiding frame in some configurations, these will be referred to as "relatively movable elements", and the opening and closing of the jaws as "relative movement".

In some embodiments, the levers 320 and 322 can be used to independently open and close the jaws of the grabber, so that, for example, pressing the levers 320 and 322 towards grip 316 will result in the jaws 542 and 552 closing together.

Here, for example, the guided frame could be attached to 550 at the point (not on 550) where the jaws would contact when both levers were fully depressed. A disadvantage of this use of the lever controllers 320 and 322 and the guided frame attachment point is that if the jaw opening distance is large relative to critical distances, it can be difficult to sufficiently accurately estimate the point where the jaws will meet (that is, the guided frame point of this example), and therefore difficult for the surgeon to appropriately position the jaws 542 and 552 before closing. It should be understood that this frame attachment point is not excluded from various embodiments described herein, although other attachments can be used as described herein.

Instead, an advantageous approach for some circumstances is to attach the guided frame to one of the movable elements of the end effector, as exemplified by frame 540 attached to 542. Here, also only the lever that moves element 352 is active, and element 342 is kept in such a position that element 352 may be closed against it by the action of the lever. With the guiding frame attached as shown, the surgeon can position element 542 directly at the desired location, and then close the jaws so that element 552 moves to location 554.

In some embodiments, the approach taken here is then analogous to how forceps are often used in freehand microsurgery, where the forceps are held in the hand. Here, the side of the forceps held by the fingers can be stabilized by the entire hand and tends to be better supported than the side with the thumb, motivating asymmetric closure during some freehand operations.

The frame may also be attached at the point on jaw 542 where the two jaws will contact when closed, as shown in FIG. 5B. Additionally, the frame may be attached so as to be parallel to the tangent of the jaw 542 at the point where the two jaws will contact. This may be advantageous as objects that are grasped will tend to align with the tangent, establishing this as a good "forward" direction to move the tool; and, rotations about the x-axis may also be advantageous. In other circumstances it may be preferable to align the x-axis with the long axis of jaw 542 (not shown, but similar to frame 520).

In some embodiments, frame 556 is attached to, but offset from, jaw 542, with the x-axis parallel to the tangent of the surface of the jaw. For example, this can be useful for working with arced suture needles. If the distance from the origin of the frame 556 to the jaw is approximately the radius of the arc of the suture needle and a suture needle that is clasped in the jaw near the point marked 544 (in an orientation so that it lies approximately in the y-z plane of frame 540 with the center of the arc near the origin of the frame—a natural way to grab a suture needle), then rotation about the x-axis of frame 556 (which can be done in R-mode) will cause the suture needle path to follow its own arc, helping to minimize pulling and other trauma to the pierced tissue.

As a non-limiting example, the following is a list of steps a surgeon could take to begin to apply a suture, where the suture is initially lying on a surface: 1) switch to R-mode and orient the grasper appropriately to pick up a suture needle; 2) in T-mode, move the jaws so that jaw with the attached frame 542 is touching the needle where it should be grasped; 3) close the jaws using lever 320; 4) switching between R and T-modes, position and orient the needle to where it would penetrate the tissue; 4) either use T-mode to push the needle through the tissue or use R-mode with a suturing frame such as 556. One advantage of this approach can be visualized from steps 2 and 3: here, when the jaws are closed, the needle is braced against the guided jaw and the only moving part is the non-guided side; but if both jaws were being controlled by levers, the needle could be accidentally moved. Accordingly, the methods and devices described herein can prevent accidental movement.

FIG. 5C shows an example having an end effector with two movable elements, 574 and 576, which could, for example, represent the blades of scissors, and which can be moved by the controller in relation to 582 by robotic control. Herein and below, the movable elements 574 and 576 will be referred to as blades for convenience.

In some embodiments, the levers 320 and 322 can be used to independently open and close the blades of the scissors, where generally pressing the levers 320 and 322 towards grip 316 will result in the blades 574 and 576 closing together, as shown by FIG. 5C. Here, for example, the guided frame could be attached to the point in space where the blades would contact when both levers were fully closed.

In some embodiments, the device is configured to set the guided frame to always stay symmetrically located between the blades, as shown with frame 570, where the origin is on the bisector between the blades and the x-axis is aligned with the bisector. For example, under single lever control, such as, 320, this could be done by having both blades advance according to the lever position.

An alternative frame is 572 which is attached to blade 574 but moves with the point of the "V" formed by the intersection between the two blades, and having the x-axis of 574 aligned with the bisector between the blades. Here, as the blades come together, the frame moves so that the origin of the frame stays with the intersection of the blades. This can be useful, for example, when turning while cutting when in R-mode, so that fixed point of the turn stays at the cutting intersection between the tissue and the blades. These frames could also be also be implemented when the blades are independently controlled, for example, when using levers 320 and 322. Another alternative frame is to attach to a cutting edge of the blade (not shown), similar to frame 540. This can be useful, for example, to allow more direct control of the blade with the attached frame so that it is less likely to damage nearby tissue.

In some embodiments, Frame selector 432 is configured to provide a way for the surgeon to select a frame for an end effector, and possibly change frames for a given end effector to suit a particular task. As a non-limiting example, each end effector could have a set of pre-established available frames, and the details of these frames are stored in the frame selector 432 selector and this information is communicated to the joint position planner 458. Information about which end effector is in use is communicated to the frame selector 432 by the joint position planner 458 so that the operator may be presented with a selection of frames to choose based on the end effector in use. The selection input can be anything that allows the surgeon to select between different frames, such as a multi-position switch, a graphical user interface, a voice recognition system, or any other means for selecting.

Furthermore, options in the frame selector may include rotational restrictions. For example, when using frame 556 to rotate a suture needle, only rotation about the x-axis is useful for this task, and rotations about other axes might be damaging, so for frame 556, in some embodiments, the frame selector may be configured with an additional constraint that rotation be restricted to be about only the x-axis. Both one-dimensional and two-dimensional rotational constraints can be made available. Furthermore, it should be understood, that if rotation is restricted to one-dimension, that is, rotation about an axis, than any two frames are operationally equivalent if the rotation axes of the two frames are collinear.

In some embodiments, each end effector may have an assigned default frame that can be automatically selected when the arm with the end effector is installed. In some embodiments, a location for the default frame would be at tip of the tool on the side most commonly in contact with tissue, and for doubly jawed tools grasping-type tools, on the side of the end effector corresponding to the finger side (e.g. negative y-axis of the guiding frame 360 for the right hand); and for scissor-type end effectors, along the bisector between the blades; though other options are choices are clearly reasonable as well. For the avoidance of doubt, the frame selector is not required, and each end effector could have a single default frame that would be the only frame used for the end effector.

In some embodiments, markings used to identify optional frame locations on tool could aid the surgeon in selecting a frame for a given task. For example, the dots 544-548 could be referenced by the frame selector 432 to help the surgeon select a frame (not shown), related to any of these points. For example, if a straight pin were held in the jaws near dot 547 and oriented perpendicular to the plane of the figure, the frame selector could have an option to select a frame with origin located near the dot 547 (for example, indicated to the surgeon as the $4^{th}$ dot from the tip). If this were selected, the end effector could then be rotated in R-mode with only small resulting translation of the pin.

Figure 6:
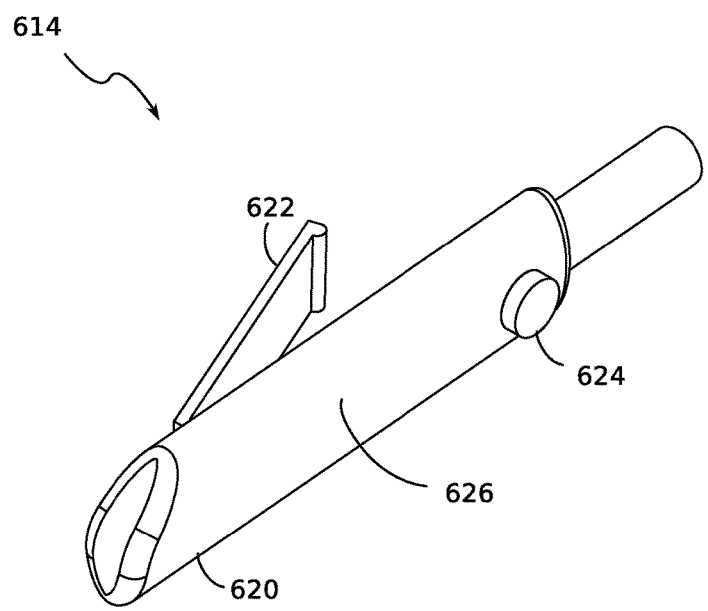
FIG. 6 illustrates a non-limiting example of a controller.

In some embodiments, for the example frame locations described above, the frames are defined relative to one or both of the moveable elements of the end effectors. For end effectors with two movable elements, this implies that there is only one degree of freedom for the two movable elements for how the elements may be opened and closed. Therefore, only one lever was required to operate the moveable elements on the end effector, and it therefore leads to an alternate embodiment of grip to 180 to only include a single lever, shown in FIG. 6 as grip 614. That is, this grip is similar to grip 180 in FIG. 3, but with the lever 322 removed with lever 622 remaining. Although this is non-limiting, an advantage of this grip is that is allows for a solid resting surface 626 for one or more fingers or the thumb if used with the left hand. Item 624 represents a button that, depending on the specific configuration, could be depressed to activate R-mode, T-mode, G-mode, or Null-mode, for example. In one aspect, this grip is well suited for the right hand as it allows for the fingers to be positioned along surface 626.

In some embodiments, it may be difficult for the operator to hold the grip 316 sufficiently stationary while the lever 320 is being depressed to close the end effector. In some embodiments, the operator can use the Null-mode switch 422. In some embodiments, functionality can be incorporated into levers 320 or 622 that will lock motion of the slave arm and end effector while lever 320 or 622 is being pressed. In some embodiments, the lever may work to lock the motion of the end effector during the major part of its motion, wherein the lever 320 or 622 is configured so that an initial light depression of the lever 320 or 622 engages the Null-mode, and continued depression of the lever 320 or 622 closes the end effector and the lever reaches the end of its motion. Additionally, in some embodiments, a force sensor can be incorporated into the lever or be otherwise in contact with the lever sufficient to measure an increase in force, so that when the lever was further pressed to increase the force beyond a threshold level, the Null-mode would be released.

The processing associated with this function can, for example, be carried out in the end effector processor 464.

As described herein, in some embodiments, the device comprises switches to configure the device. These are illustrated as a non-limiting example as 422, 424, and 426. The configuration, can for example, make a few approaches of operation, fairly easily accessible, which may find use in specific surgeries. As a first approach, the surgeon would use the G-mode for general surgery, and the decoupled M-state, for microsurgery; and in this case, often staying in either mode for fairly extended periods. Continuing with this first approach, most of the rapid switching could quickly be done between T-mode and R-mode using a single selection of switch 424. In a second approach, the surgeon could use the G-mode for general and microsurgery, but could do rotations of the end effector in R-mode. In this case, switch 424 could be set and left in R-mode, and the switch 426 could be used to switch between G-mode and the M-state (effectively R-mode) with a single selection. That is, both of these approaches allow for switching between the commonly used modes with a single switch, and there is an advantage to being able to switch modes quickly and easily with a single selection.

However, the modes can be configured by other mechanisms than those described hereinbefore to achieve the same result. Therefore, many other switch configurations are clearly possible and reasonable. For example, there could be a single momentary contract foot switch to enter R-mode, wherein the system stays in R-mode while the switch is depressed, and leaves R-mode when the switch is released. In some embodiments, the device comprises a single switch which cyclically moves through the modes, G, R, T, G, R, and the like. In some embodiments, the device comprises a single switch which cyclically moves through the modes, G, R, T, Null, G, R, T, Null, G, and the like. In some embodiments, only two of the modes from the set G-mode, T-mode, and R-mode, are present; and a single switch selects between these two modes.

Furthermore, the switches 422, 424, 426, 428, 430, and 432, and any switched inputs mentioned hereinbefore, could be selected from any type of input known to those familiar with control systems; and, for example, can be selected independently from any of foot switches, finger operated switches, finger operated switches on or near master controller, graphical user interface systems, voice recognition systems, and the like.

The switch configurations, for example, 422, 424, and 426, provided hereinbefore should be understood to not be limiting to the scope of the embodiments described herein. Although it should be understood to be non-limiting, it should also be understood that, in some embodiments, for convenient usage, a system where the surgeon can, for example, switch reasonably quickly and conveniently between at least two of the modes from the set G-mode, R-mode, and T-mode, using one, two, or three actions (by actions such as, activating switch settings, speaking words, and the like) and, additionally, in some embodiments, without the surgeon removing their eyes from the surgical scene, is generally advantageous.

In some embodiments, a single master control 310 can be used for G-mode, R-mode, and T-mode. That is, in some embodiments, one uses the 6-DoF control 310 and alternately maps inputs to the control to either guide generalized, pure rotational, or pure translational motions of the slave tool. This has an advantage in that it provides quick and easy access to multiple modes. For example, the motion of grip 316, and hence the guiding frame 360, that would cause rotation of the end effector is the same in both G-mode and R-mode. That is, in G-mode, when the operator attempts to guide a pure rotation, the result of the slave will usually be a rotational motion with some amount of translational error; and in R-mode, this same motion will result in the same rotation as in G-mode, but just without the translational error. A similar outcome holds for G-mode compared to T-mode. These operations are generally intuitive and may be quickly learned.

It should be understood that the embodiments described herein are not limited to any particular master control. In particular, using decoupled control for rotation and translation can be applied across a wide range of human input devices (HIDs) that can be used as master controllers, and the improvement in precision is not reliant on a particular mechanism of input. There are a wide range of HIDs in use, and, in practice, many work well for providing usable and accurate control, and many different types of mappings from input to output already exist in the art and are found to be reasonably intuitive to the operator. Furthermore, for the master controller 310 presented herein, it was reasonable to convert the rotation of the guided frame 360 to the rotational control channel 442, and the translation of the guided frame 360 to the translational control channel 440, but this is not necessary. That is, channels 442 and 440 carry information to direct the rotation and translation of the guided frame, but it is not generally necessary that this information results from rotation and translation of the master frame. For example, it is common, and generally perceived to be intuitive, to use rotation to guide a translation, and vice versa, in a range of human interface devices. For example, the scroll wheel on a computer mouse rotates (that is, undergoes a physical rotation), but is commonly used to scroll graphics in a display (that is, a linear translation); 2D translational motion of a cursor on a screen can be guided using a stationary rolling ball as a computer mouse; and many software computer aided design (CAD) systems allow the user to select whether motion of the mouse (commonly a translational motion) controls either translation or rotation.

Considering the foregoing, embodiments are provided herein for alternative input systems, though it should be understood that this list is not limiting, but instead exemplifies a few of the many possible options.

In some embodiments, different physical controls could be used to guide different modes. For example, a first master control with a first set of sensors could guide G-mode; a second master control having a second set of sensors could be used to guide T-mode; and a third master control having a third set of sensors could be used to guide R-mode; wherein these are configured so that use of one master controller by the surgeon does not affect sensor readings from another. In some embodiments of methods for using this system, the surgeon would shift their hand from one control to the other. The inputs to the component analogous to the joint motion planner 458 of the previous embodiment, could be selected simply on which master controller was being used. In some embodiments, methods for using this system, different hands and/or fingers could simultaneously operate different master controls for the same end effector, for example, one control for rotation and a separate control for translation.

It should be understood that to gain the advantages of decoupling, it is not required that the inputs to T-mode, R-mode, and/or G-mode alternate in time; but it should be understood that alternating in time is just one approach to making the inputs independent (so that, for example, directive action from the surgeon to the master controller that was intended to guide rotation did not also influence the translation). Furthermore, it should be understood that having a generalized motion mode (G-mode) is not required in this invention, and that a system with only pure rotational control and pure translational control would allow for decoupled control. For the avoidance of doubt, a device can have multiple modes or only one mode. In some embodiments, it has a G, R, or T mode in any combination. For example, a device could be configured to have a R and T mode with no G mode, or a R mode with a G mode, a R mode and T mode, a T mode with a G mode, only a R mode, or only a T mode. Thus, the device can be configured in any configuration that fits the operator's needs. These are non-limiting examples.

Figure 7:
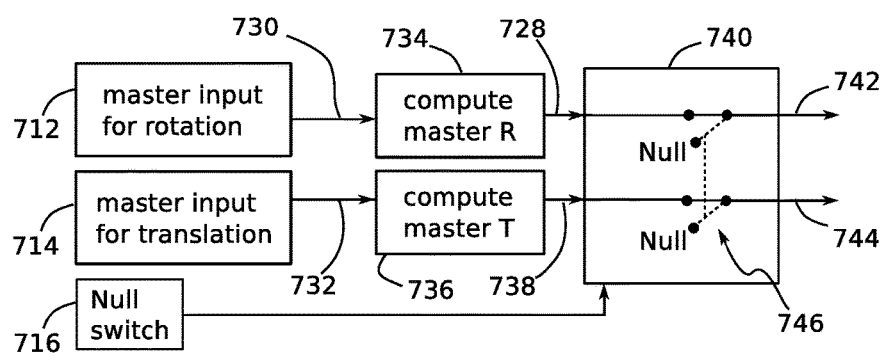
FIG. 7 illustrates a non-limiting schematic representation of an overview of an embodiment

A partial schematic for some embodiments is shown in FIG. 7. Here there are two independent master controllers, a first master controller that controls rotation of the end effector frame 712, and a second master controller that controls translation of the end effector frame 714, and two master input channels 730 and 732 (replacing the single channel 436) that contain sensor data from the master controllers 712 and 714. Sensor data on 730 is transformed by subprocessor 734 into data representing the rotational control information for the end effector, and sensor data on 732 is transformed by subprocessor 736 into data representing the translational control information for the end effector in channel 738. Subprocessor 740 effects the Null switch, where the double throw switch 746 schematically represents either passing both input channels through or sending a Null signal as directed by Null switch 716. Channels 742 and 744 emerging from the subprocessor 740 are then processed analogous to channels 456 and 454 in FIG. 4. As mentioned generally hereinbefore, it should be understood that the master controllers for rotation 712 and translation 714 need not have embodiments that involve a mechanical input mechanism for rotation and translation that would be performed by the surgeon (operator). One advantage, but not the only advantage, is that both rotation and translation of the end effector could be simultaneously controlled, but that the control would be decoupled as described herein. For example, in this configuration, if the surgeon were to only provide input to one of the master controllers, for example, the first (rotation) controller, but not provide any input into the second, then the end effector frame would only rotate but not translate, similar to R-mode behavior. Also, though, the surgeon could simultaneously guide both the first and the second master controller to produce a generalized motion of the guided frame but with the precision of the decoupled mode. An advantage of this embodiment is that each of the first and the second master controllers need only have 3-DoF, since each is only independently controlling translation or rotation.

In some embodiments, a single 3-DoF controller can be used to guide both translation and rotation of the end-effector, and a switch similar to 424 could be used to determine whether the control was used to guide rotation or translation of the end effector frame at a given moment.

It should also be understood that many different types of sensors can be used to read guiding directives from the surgeon, and that many devices sufficient to control a guided frame are known in the art. For example, alternate mechanical and sensor configurations could be used that are different from the arrangement in FIG. 3, and many such systems are known in the art, with several mentioned hereinbefore. Optical tracking of a tool held in the hand, with or without visible reference marks. An empty hand could also be optically tracked, and information extracted to control translation and rotation, such as the average position and rotation of reference points on the hand, or motions thereof. Furthermore, it is not required that the master controller move, but the controller could instead, for example, use force sensor and/or strain sensors with a substantially rigid master controller; then, rather than use motion of master attached frame, forces and/or torques relative the attached frame could be used. For the master controller of FIG. 3, as mentioned hereinbefore, using forward kinematics is one non-limiting method of calculating information about the guiding frame, but for systems without rigid elements and joint sensors, other means are known in the art. For example, for systems that track multiple reference points in space, kinematic quantities can be determined from these points, and, for example, the rotation of a solid body can generally be calculated from three non-collinear points (for example, chapter 8 in Fundamentals of Robotic Mechanical Systems by Jorge Angeles, which is hereby incorporated by reference.)

Furthermore, it is not required that either rotation or translation be controlled with a full 3-DoF controller, or that the end effector have a full 3-DoF in either position or orientation. It can be more intuitive, for example, if the degrees of freedom of the control be at least sufficient to meet the degrees of freedom of motion of the tool, but this is not a requirement. In some embodiments, it can be common for end effectors to not have a full 3-DoF range of rotational motion, and for these cases, a master controller for rotation that only controls the available DoF of the end effector may be more intuitive for the surgeon. It should be understood, that, for example, if the end effector can rotate in any capacity, then controlling this rotation with a control that is decoupled from translational control may lead to improved precision. Even for end effectors with a full 6-DoF, all 6-DoF will not always be fully achievable at each position and orientation, but here too, the possible precision benefits of decoupled control are still relevant. It should be apparent that benefits of decoupled control can be applied to systems with fewer than 3-DoF of translation and/or fewer 3-DoF of rotation for the end-effector. If the tool can be rotated or translated at all, doing so in a decoupled mode, and the ability of the operator to easily and quickly switch into and out of one or both of these modes, can improve precision and operability. The description of an effector or system with either 6-DoF or 3-DoF is simply exemplary. The systems and devices described herein can be used with any type of system having two or more degrees of freedom. For example, a grasper can be referred to as having 7-DoF (i.e., 3 translation, 3 rotation, and 1 for jaw position). The system described herein can also be used with such an effector or device. In some embodiments, the system and device described herein can also be used to control motion with 5-DoF, for example, when controlling a pin or a rod which is symmetrical about the long axis so that rotation about this axis may not need to be controlled. Thus, for example, many robotic arms and end effectors known in the art have fewer than 6-DoF in translation and rotation, and the device and system described here can also be used to control this type of end effectors. Additionally, the system can be used to control an effector on a flat surface where a third degree of rotation is not applicable. Accordingly, the degrees of freedom should not be construed to be limiting.

In some embodiments, a scaling factor is incorporated for translation but not for rotation. In some embodiments, a scaling factor is incorporated for rotation but not for translation. In some embodiments, a scaling factor for rotation or translation can be used, and its absence above should not be interpreted as limiting. Furthermore, filtering designed to filter out hand tremor can also be incorporated, for example, along input channel 436. Methods and sensors to filter tremors are known to one of skill in the art and can be incorporated into the devices described herein.

For example, in some embodiments, temporal filtering to reduce the effects of tremor can be included. In some embodiments, temporal filtering to reduce the effects of tremor is not included. It is to be understood that the filtering could be included. For example, in some embodiments, a distinct use of temporal filtering, for systems where the rotation and translation channels (for example, 456 and 454) represent physical rotation and translation of the master control, it may be useful to apply the temporal filter separately to these channels, using separate parameters for each filter, as the tremor for rotational and translational motions may have different temporal properties.

In some embodiments, for tasks where it is desirable to drive rotation and translation in a deterministically coupled way, the surgeon can control a first independently controlled motion (that is, one of rotation and translation), and the second can be driven by the processor 140 to follow in a preset way from the first motion. For example, in cutting a shape with scissors or scalpel, the translational motion of the tool may determine the preferred orientation of the tool (here, for example, aligned with the tangent of the path of the tool), so that the surgeon could control the translation, and the orientation could be configured to automatically assume the appropriate angle.

It should be understood that the embodiments do not require perfectly pure translation or rotation of end effector. Instead, the focus of decoupled control is on reducing the consequence of human error in controlling precision motion. Cases where kinematic restrictions, or other reasons make it preferable to allow for small rotations of the end effector while it is being translated should be considered within the scope of this invention. Furthermore, for many applications a rotation of ±10°, for example, will be acceptable. Similarly, in some embodiments, inaccuracies in maintaining a perfectly pure rotation of the end effector due to limitations of the slave arm and controller should also be considered consistent with this invention.

In some embodiments, the master controller is rigidly or flexibly mechanically connected to a portion of the robot arm that is mechanically connected to the end effector. In some embodiments, the master controller is not mechanically connected to the robot arm that is mechanically connected to the end effector.

In some embodiments, an operator may use applied forces and/or motions to provide input to the master controller, and a subset of applied forces and/or motions will be referred to as a "gesture". It should be understood that a gesture comprises a subset of the forces and/or motions produced by an operator, but not necessarily all forces and/or motions, so that, for example, one hand could produce a first gesture while the other hand a second gesture; or that one finger could produce third gesture and another finger forth gesture; or that a gesture could consist of a combination of inputs from various hands and/or fingers, or other operator directed body parts or actions. In some embodiments, a master-slave robotic system maps gestures (supplied by the operator) to motions of the end effector.

In some embodiments, a decoupled mode has at least one of two aspects: 1) a rotation mode of input (R-mode), where a gesture directs the slave tool through pure rotation; and, 2) a translation mode of input (T-mode), where a gesture directs the slave tool through pure translation. In some embodiments, the decoupled mode should be consistent with practical application of the gestures applied by the surgeon to influence the master controller. Whereas many systems would allow for a theoretical decoupling if gestures were applied in an idealized and possibly impractical way, here the decoupled mode refers to a system wherein reasonable variation of a subset of the gestures or a combination of gestures serve to guide the slave tool in only one of translation or rotation. By "reasonable variation," it should be understood that without the surgeon or operator paying extremely high level of attention to the applied forces and/or motions, the guidance from these forces and/or motions serves to direct only one of rotation and translation. In practice, for most of the working range of forces applied at a set of points to the control system, variation in any of the forces in any direction by 10, 3, 1, 0.3, 0.1, 0.03, or 0.01 Newton, for example, or variation in any of the motions in any direction by 10, 3, 1, 0.3, 0.1, or 0.03 mm should not change whether the guiding is exclusive to rotation or translation. Furthermore, it should also be understood that by "direct the slave tool through pure rotation" or "direct the slave tool through pure translation" it is meant that variations in the forces and/or motions that direct one (say, rotation) do not affect the other (say, translation), but they may be combined to direct the motion of the end effector in both translation and rotation (as would be the case with physically disconnected rotation and translation control systems).

In some embodiments, the decoupled control can be used for improving precision control. Some of the embodiments described herein can be distinguished from other decoupled systems in at least one or more of the following aspects: 1) the system is decoupled to have at least one of a pure rotational control input and pure translational control input; 2) by "precision control" in one aspect, this should be understood to refer to a configuration wherein, under pure rotation there would be a fixed point of rotation on or near the working part of the end effector (that is, the part meant to contact the object, such as the patient, tissue, sample, etc.), and/or the most distal portion of the end effector (the tip of the end effector), and that, depending on the requirements of a task, the fixed point could be within 5 mm, 1 mm, 0.3 mm, 0.1 mm, or 0.05 mm, or be within $1/10^{th}$, $1/20^{th}$, $1/50^{th}$, $1/100^{th}$, $1/200^{th}$, $1/500^{th}$, $1/1000^{th}$, $1/1000^{th}$, $1/2000^{th}$, $1/5000^{th}$, $1/10000^{th}$, $1/20000^{th}$, $1/50000^{th}$, $1/100000^{th}$ of the control span, of the working part or most distal portion of the end effector.

In some embodiments, one way to distinguish a system with decoupled control is one wherein, given two identical gestures applied to a master control of a master-slave type of system, then the system could be considered to have a decoupled mode when the state of the system can be set so that the identical gestures maps to a different selection from the set of: a generalized motion, a pure rotational motion, and a pure translational motion of an end effector.

The disclosures of each and every patent, patent application, and publication cited herein are hereby incorporated herein by reference in their entirety and for their intended purpose. While there has been disclosed various embodiments, it is apparent that other embodiments and variations may be devised by others skilled in the art without departing from the true spirit and scope of those disclosed herein.

What is claimed is:

1. A device comprising a controller, a sensor assembly, a processor, an end effector, and one or more switches, wherein:

the controller is operatively connected to the sensor assembly and the end effector;

the processor is operatively connected to the sensor assembly, and the end effector, wherein the processor is configured to receive one or more inputs from the sensor assembly and to provide a rotational output command and/or a translational output command, based upon the one or more inputs, to the end effector to control rotational movement and/or translational movement of the end effector;

the processor is operatively connected to the switches, wherein the switches control output of the rotational output command and the translational output command; and the end effector is configured to rotate about a fixed point of rotation positioned at or approximately at the tip of the end effector, wherein the fixed point of rotation translates with the translational movement of the end effector.

2. The device of claim 1, wherein one or more of the switches are configured to select one of the rotational command and the translational command to control movement of the end effector.

3. The device of claim 1, wherein the sensor assembly is configured to measure the revolute displacements and/or the linear displacements of the controller.

4. The device of claim 1, wherein the processor is configured to determine the rotational and translational movement of the controller and the processor is configured to communicate with the end effector to move the end effector in a rotational movement and/or a translational movement.

5. The device of claim 1, wherein the processor is configured to communicate with the end effector to move the end effector in a rotational movement that is significantly free of any translational movement or the processor is configured to communicate with the end effector to move the end effector in a translational movement that is significantly free of any rotational movement.

6. The device of claim 1, wherein the one or more switches is configured to so that the end effector rotational movement is significantly free of any translational movement.

7. The device of claim 1, wherein the one or more switches is configured so that the end effector translational movement is significantly free of any rotational movement.

8. The device of claim 1, wherein the device is configured such that a force or motion applied to the controller moves the end effector through pure translation or pure rotation.

9. The device of claim 1, wherein the controller comprises a grip and system of connecting elements and movable joints that allow the grip to be moved in at least six degrees of freedom (6-DoF) where three degrees of freedom (3-DoF) correspond to the position of the controller, and 3-DoF correspond to the orientation of the controller.

10. The device of claim 9, wherein the sensor assembly is configured to receive inputs from the controller to determine the position of the controller and the orientation of the controller.

11. The device of claim 10, wherein the processor is configured to receive inputs from the sensor assembly to determine the rotational movement of the controller and/or the translational movement of the controller.

12. The device of claim 11, wherein the processor is configured to output the rotational movement of the controller and/or the translational movement of the controller to the end effector to move the end effector in a rotational movement and/or translational movement.

13. The device of claim 11, wherein the processor is configured to output the rotational movement of the controller to the end effector through a first communication channel and to output the translational movement of the controller to the end effector through a second communication channel.

14. The device of claim 11, wherein the processor is configured to output the rotational movement of the controller and/or the translational movement of the controller to the end effector to move the end effector in a translational movement that is significantly free of any rotational movement or a rotational movement that is significantly free of any translational movement.

15. The device of claim 11, wherein the device is configured to move the end effector in a rotational movement that is significantly free of any translational movement or wherein the device is configured to move the end effector in a translational movement that is significantly free of any rotational movement.

16. The device of claim 15, wherein the one or more switches configures the device to move the end effector in a rotational movement that is significantly free of any translational movement or wherein the one or more switches configures the device to move the end effector in a translational movement that is significantly free of any rotational movement.

17. A method of moving an end effector in a translational movement that is significantly free of any rotational movement or in a rotational movement that is significantly free of any translational movement, wherein a controller is operatively connected to the end effector, the method comprising:

sensing a force and/or motion input applied to the controller via a sensor assembly;

transmitting the force and/or motion input from the sensor assembly to a processor in communication with the sensor assembly;

analyzing the force and/or motion input via the processor to decouple the rotational movement and the translational movement into a rotational output command and a translational output command; and transmitting the rotational output command and/or the translational output command to the end effector to move the end effector in a translational movement that is significantly free of any rotational movement or in a rotational movement that is significantly free of any translational movement;

wherein the rotation of the end effector is about a fixed point of rotation positioned at or approximately at the tip of the end effector, and wherein the fixed point of rotation translates with the translational movement of the end effector.

18. The method of claim 17, wherein the controller is associated with a device comprising one or more switches, wherein the one or more switches are configured to control the transmission of the rotational output command and/or the translational output command, wherein the one or more switches prevent the transmission of the rotational output command and/or the translational output command to the end effector.

19. A method of moving an end effector, wherein a device comprising at least a first controller and a second controller are operatively connected to the end effector, the method comprising:

sensing a force and/or motion input applied to the first controller and the second controller via a sensor assembly;

transmitting the force and/or motion input from the sensor assembly to a processor in communication with the sensor assembly;

analyzing the force and/or motion input via the processor to produce a rotational movement and the translational movement from the first controller and the second controller into a first controller rotational output command, a first controller translational output command, a second controller rotational output command, and a second controller translational output command; and transmitting the first controller rotational output command and/or the first controller translational output command to the end effector to move the end effector in a translational movement that is significantly free of any rotational movement or in a rotational movement that is significantly free of any translational movement; and/or transmitting the second controller rotational output command and/or second controller the translational output command to the end effector to move the end effector in a translational movement that is significantly free of any rotational movement or in a rotational movement that is significantly free of any translational movement;

wherein the rotation of the end effector is about a fixed point of rotation positioned at or approximately at the tip of the end effector, and wherein the fixed point of rotation translates with the translational movement of the end effector.

20. A device comprising a sensor assembly, a processor, an end effector comprising a pair of jaws comprising a first jaw and a second jaw, a first switch, a second switch, and a controller comprising a grip and a system of connecting elements and movable joints that allow the grip to be moved in at least six degrees of freedom where three degrees of freedom correspond to the position of the controller, and three degrees of freedom correspond to the orientation of the controller, wherein:

the controller is operatively connected to the sensor assembly and the end effector;

the sensor assembly is configured to receive inputs from the controller to measure the revolute movements and/or the linear movement of the controller;

the processor is operatively connected to the sensor assembly, the first switch, the second switch, and the end effector, wherein the processor is configured to receive one or more inputs from the sensor assembly to determine the rotational movement of the controller and/or the translational movement of the controller, and to provide a rotational output command and/or a translational output command, based upon the one or more inputs, to the end effector to control rotational movement and/or translational movement of the end effector;

the first switch controls output of the rotational output command and the second switch controls output of the translational output command; and the end effector is configured to move in a rotational movement that is significantly free of any translational movement or in a translational movement that is significantly free of any rotational movement, wherein the end effector is configured to rotate with at least two degrees of freedom about a fixed point of rotation positioned at or approximately at a point on the first jaw where the pair of jaws will contact when in a closed position, and wherein the fixed point of rotation translates with the translational movement of the end effector.

\* \* \* \* \*